US005597893A

United States Patent [19]
Baker et al.

[11] Patent Number: 5,597,893
[45] Date of Patent: Jan. 28, 1997

[54] PREPARATION OF STABLE INSULIN ANALOG CRYSTALS

[75] Inventors: Jeffrey C. Baker, Indianapolis; Bradley M. Roberts, Greenwood, both of Ind.

[73] Assignee: Eli Lilly and Company, Indianapolis, Ind.

[21] Appl. No.: 332,296

[22] Filed: Oct. 31, 1994

[51] Int. Cl.$^6$ .............................. A61K 38/28; C07K 14/62
[52] U.S. Cl. ............................................ 530/304; 530/324
[58] Field of Search .................................. 530/303, 304, 530/305; 514/3

[56] References Cited

U.S. PATENT DOCUMENTS

| | | | |
|---|---|---|---|
| 2,143,590 | 1/1939 | Scott et al. | 167/75 |
| 2,626,228 | 1/1953 | Petersen | 167/75 |
| 2,920,014 | 1/1960 | Petersen et al. | 167/75 |
| 3,719,655 | 3/1973 | Jackson | 260/112.7 |
| 3,856,771 | 12/1974 | Jackson | 260/112.7 |
| 4,959,351 | 9/1990 | Grau | 514/4 |
| 5,028,587 | 7/1991 | Dörschug et al. | 514/3 |
| 5,149,777 | 9/1992 | Hansen et al. | 530/303 |
| 5,164,366 | 11/1992 | Balschmidt et al. | 514/3 |

FOREIGN PATENT DOCUMENTS

| | | |
|---|---|---|
| 0214826 | 3/1987 | European Pat. Off. . |
| 0375437 | 6/1990 | European Pat. Off. . |
| 0383472 | 8/1990 | European Pat. Off. . |

OTHER PUBLICATIONS

Howey, et al., *Diabetes*, 43, 396–402 (Mar. 1994).
*Diabetes*, 41, Suppl. 1, 192A (1992).
Brems, et al., *Protein Engineering*, 5:6, 519–525 (1992).
Heinemann, et al., *Diabetologia*, 33, 384–386 (1990).
Kirk–Othmer, *Encyclopedia of Chemical Technology*, 13, 607–614 (1981).
Bruce H. Frank, Text and Slide copies of lecture given at the Conference on Insulin, Self Association and Conformational Studies on Human Proinsulin and Insulin Analogs, University of York, Aug. 29–Sep. 1, 1989.
Chance et al. 08/057201 May 5, 1993.
Baker et al. 08/260,647 Jun. 16, 1994.
Bakayasa et al. 08/260,634 Jun. 16, 1994.
Fullerton, et al., *Biochim. Biophys. Acta*, 214, 141–147 (1970).
*Diabetologia*, 30, 503A (1987).
Brange, et al., *Nature*, 333:16, 679–682 (Jun. 1988).
Brange, et al., *Diabetes Care*, 13:9, 923–954 (Sep. 1990).
Brange, et al., *Structural Biology*, 1, 934–940 (1991).
Brange, *Galenics of Insulin: The Physico–chemical and Pharmaceutical Aspects of Insulin and Insulin Preparations*, Springer–Verlag Berlin Heidelberg, Germany (1987).
Scott, *Biochemical Journal*, 28:4, 1592–1602 (Apr. 28, 1934).
Brems, et al., *Protein Engineering*, 5:6, 527–533 (1992).
Wollmer, et al., *Biol. Chem. Hoppe–Seyler*, 370, 1045–1053 (Sep. 1989).
Wollmer, et al., *Phenol–Promoted Structural Transformation of Insuline in Soluntion* from the 2nd Assisi International Symposium on Advanced Models for the Therapy of Insulin–Dependent Diabetes, 903–911 (Apr. 1986).
Harding, et al., *The Crystal Structure of Insulin: II. An Investigation of Rhombohedral Zinc Insulin Crystals and a Report of Other Crystalline Forms*, Chemical Crystallography Laboratory, South Parks Road, Oxford, England (Nov. 8, 1965).
Derewenda, et al., *Nature*, 338, 594–596 (Apr. 13, 1989).
Brems, et al., *Protein Engineering*, 5:6, 519–525 (1992).
Abel, *Proc. Nat'l Acad. Sci. U.S.*, 12:132 (1926).

*Primary Examiner*—Michael P. Woodward
*Assistant Examiner*—Benet Prickril
*Attorney, Agent, or Firm*—Ronald S. Maciak; Steven C. Caltrider; David E. Boone

[57] ABSTRACT

The present invention discloses a process of preparing a crystalline alkali metal or ammonium salt of $Lys^{B28}Pro^{B29}$-human insulin. The process is useful in the purification and manufacture of $Lys^{B28}Pro^{B29}$-human insulin. $Lys^{B28}Pro^{B29}$-human insulin is useful in the treatment of diabetes.

9 Claims, No Drawings

PREPARATION OF STABLE INSULIN ANALOG CRYSTALS

FIELD OF INVENTION

The present invention relates to a monomeric analog of human insulin. More specifically, the present invention relates to a process of preparing a crystalline insulin analog. The process is useful in the purification and manufacture of $Lys^{B28}Pro^{B29}$-human insulin. $Lys^{B28}Pro^{B29}$-human insulin is useful in the treatment of diabetes.

BACKGROUND OF THE INVENTION

Since the introduction of insulin in the 1920's, continuous strides have been made to improve the treatment off diabetes mellitus. Major advances have been made in insulin purity and availability. Various formulations with different time-actions have also been developed. Despite these improvements, subcutaneous injection therapy still falls short of providing the patient with convenient regulation and normalized glycemic control. Frequent excursions from normal glycemia levels over a patient's lifetime lead to hyper- or hypoglycemia, and long term complications including retinopathy, neuropathy, nephropathy, and micro- and macroangiopathy.

To help avoid extreme glycemic levels, diabetics often practice multiple injection therapy whereby insulin is administered with each meal. However, this therapy has not yet been optimized. The most rapid-acting insulin commercially available peaks too late after injection and lasts too long to optimally control glucose levels. Recently, considerable effort has been devoted to create insulin formulations and insulin analog formulations that alter the kinetics of the subcutaneous absorption process.

Because all commercial pharmaceutical formulations of insulin contain insulin in the self-associated state and predominately in the zinc-hexamer form, it is believed that the rate-limiting step for the absorption of insulin from the subcutaneous injection depot to the bloodstream is the dissociation of the self-aggregated insulin hexamer. To accelerate this absorption process, monomeric insulin analogs have been developed. These monomeric analogs possess a comparatively more rapid onset of activity than insulin while retaining the biological activity of native human insulin. They provide a rapid absorption to place injection time and peak action of insulin into closer proximity with postprandial glucose excursion associated in the response to a meal.

The present invention provides a novel process of preparing crystals of one such monomeric analog, $Lys^{B28}Pro^{B29}$-human insulin ($Lys^{B28}Pro^{B29}$-hI). $Lys^{B28}Pro^{B29}$-hI is disclosed in U.S. patent application Ser. No. 07/388,201 (EPO publication number 383 472). However, U.S. patent application Ser. No. 07/388,201 does not disclose a commercially viable process of preparing crystalline $Lys^{B28}Pro^{B29}$-hI.

The crystallization of insulin is well known in the art. Initial discoveries date back to 1926 when Abel crystallized insulin in the isoelectric region from a solution buffered with brucine, pyridine, and ammonium acetate. Abel J. J., *Proc. Nat'l Acad. Sci. U.S.* 12: 132 (1926). Peterson, et al. in U.S. Pat. No. 2,920,104 describe insulin crystals and preparations and processes for producing them. R. L. Jackson, U.S. Pat. No. 3,719,655, discloses a process for preparing ammonium and alkali metal salts of insulin. The process comprises adjusting the basicity of a pork or beef insulin containing solution comprising pork or beef insulin and a cation selected from the group consisting of an alkali metal cation and the ammonium cation at a concentration of 0.2 molar to 1.0 molar to about pH 7.2 to about pH 10.0 with an alkali metal or ammonium base. The process has evolved commercially as the "8.2 process," that is the maximum yield of the insulin crystals is at pH 8.2. Most significantly, when $Lys^{B28}Pro^{B29}$-human insulin is subjected to the pH 8.2 conditions described in Jackson to form sodium crystals, no such crystallization occurs.

The present invention provides specific conditions under which monomeric $Lys^{B28}Pro^{B29}$-human insulin will associate and crystallize. Accordingly, the invention provides a process of crystallizing $Lys^{B28}Pro^{B29}$-hI. The process prepares high quality, high yield alkali metal or ammonium salts as crystals on a large scale. The crystals provide a stable, solid form of the molecule. Crystalline solids are particularly advantageous because they are more easily characterized, purified, and more pharmaceutically elegant than solids that are amorphous. The process is suitable for commercial application.

SUMMARY OF THE INVENTION

This invention provides a process for preparing a crystalline $Lys^{B28}Pro^{B29}$-human insulin alkali metal or ammonium salt, which comprises adjusting the pH of a solution from a pH below the isoelectric point of $Lys^{B28}Pro^{B29}$-human insulin to between about pH 8.5 to about pH 9.5 with an alkali metal or ammonium base; wherein said solution comprises about 5 mg/mL to about 50 mg/mL $Lys^{B28}Pro^{B29}$-human insulin, a pharmaceutically acceptable preservative, and an initial cation concentration of about 30 mM to about 100 mM said cation being selected from the group consisting of an alkali metal or ammonium.

DETAILED DESCRIPTION AND PREFERRED EMBODIMENTS

All amino acid abbreviations used in this disclosure are those accepted by the United States Patent & Trademark Office as set forth in 37 C.F.R. § 1.822(b)(2).

As noted above, the invention provides a process for preparing a crystalline alkali metal or ammonium salt of $Lys^{B28}Pro^{B29}$-human insulin. The term "$Lys^{B28}Pro^{B29}$-human insulin" or "$Lys^{B28}Pro^{B29}$-hI" is a fast-acting insulin analog that is less prone to dimerization or self-association. $Lys^{B28}Pro^{B29}$-hI is human insulin wherein proline at position $B^{28}$ of the B-chain is substituted with Lysine; and Lysine at position $B^{29}$ of the B-chain is substituted with Proline as described in U.S. patent application Ser. No. 07/388,201 (EPO publication number 383 472), herein incorporated by reference.

The term "isoelectric point" means the pH at which the net charge of $Lys^{B28}Pro^{B29}$-hI in solution is zero. The isoelectric point for $Lys^{B28}Pro^{B29}$-hI is about pH 5.4.

The term "pharmaceutically acceptable preservative" refers to an agent commonly employed to prevent bacterial growth in parenteral formulations. Pharmaceutically acceptable preservatives include phenol, m-cresol, resorcinol, and methyl paraben.

The term "alkali metal" is known to one skilled in the art and includes lithium, sodium, potassium, rubidium, and cesium. Preferably, an alkali metal is sodium or potassium.

The present invention discloses conditions under which $Lys^{B28}Pro^{B29}$-hI crystallizes with an alkali metal or ammonium in the presence of a preservative to form a stable, crystalline solid. The concentration of $Lys^{B28}Pro^{B29}$-hI during the crystallization is about 5 mg/mL to about 50 mg/mL. Preferably, the concentration is about 18 mg/mL to about 22 mg/mL $Lys^{B28}Pro^{B29}$-human insulin; most preferably, the concentration is about 20 mg/mL $Lys^{B28}Pro^{B29}$-hI. A solution of $Lys^{B28}Pro^{B29}$-hI is prepared by dissolving the analog in an aqueous diluent. Dissolution may be aided by what is commonly known as an acid dissolution, i.e., the pH is lowered to about 3.0 to 3.5 with a physiologically tolerated acid, preferably 0.5N to 1.0N acetic acid. Other physiologically tolerated acids include citric acid, and phosphoric acid. The selection of the acid is not critical. However, one skilled in the art would recognize that the acetate, phosphate, or citrate serves as a buffer thus facilitating the pH adjustments necessary for the crystallization. Other acids may be employed in conjunction with a physiologically tolerated buffer, such as dibasic sodium phosphate, TRIS, sodium acetate, or sodium citrate. The selection and concentration of buffer are known to one skilled in the art.

The preservative is added to the analog solution at a pH below the isoelectric point of $Lys^{B28}Pro^{B29}$-hI. Generally, the concentration of preservative is in molar excess; specifically, about 0.005 mM to about 0.05 mM. More preferably, the preservative is liquefied phenol at a concentration of 0.023 mM (0.3% by volume).

The cation concentration of the solution before the pH adjustment is about 30 mM to about 100 mM (hereinafter initial cation concentration). Preferably, the initial cation concentration is 30 mM to 50 mM. The final cation concentration is variable depending on the amount of alkali metal or ammonium used in the pH adjustment. Generally, the final cation concentration is between about 500 mM and 800 mM. The cation is selected from the group consisting of an alkali metal or ammonium. Preferably, the cation is sodium.

The pH is adjusted from below the isoelectric point of $Lys^{B28}Pro^{B29}$-human insulin to about 8.5 to about 9.5, preferably about 8.9 to about 9.1 with an alkali metal or ammonium base. The preferred alkali metal bases are sodium, ammonium, or potassium hydroxide. Most preferably, the base is sodium hydroxide.

The manner in which the $Lys^{B28}Pro^{B29}$-hI is dissolved in the diluent or the order in which the preservative, cation, and $Lys^{B28}Pro^{B29}$-hI are added to the diluent is not critical to the present process. The temperature of the crystallization is also not critical. The temperature range acceptable is from about 4° C. to about 26° C. Preferably, the temperature is about 4° C. to about 6° C.

The crystals form with, or without, agitation and may be collected and washed. Crystals prepared by the claimed process are sensitive to the washing conditions used to remove residual soluble protein. Therefore, the crystals are preferably washed in sodium acetate to prevent re-dissolution. Preferably, the crystallization is carried out with agitation.

$Lys^{B28}Pro^{B29}$-hI may be recrystallized, if required, to facilitate filtration. The crystals may be collected and dried by conventional means. The crystals prepared according to the present invention are high quality and in high yield on a commercial scale. The crystals provide a stable solid form of the bulk drug substance suitable for holding and dispensing to fill/finish operations. The crystallization procedure does not alter the purity or aggregation kinetics of the material.

Most significantly, the crystallization conditions are sensitive to the selection of preservative, base and cation concentration; that is, one skilled in the art carrying out the process would adjust the parameters defined herein to achieve well-defined crystals. The optimum conditions for each preservative-cation-base combination varies within the ranges disclosed.

The formation of crystalline pork or beef insulin has been extensively studied. Jackson, U.S. Pat. No. 3,719,655, discloses a process for preparing ammonium and alkali metal salts of beef or pork insulin. The process comprises adjusting the basicity of a pork or beef insulin containing solution comprising pork or beef insulin and a cation selected from the group consisting of an alkali metal cation and an ammonium cation at a concentration of 0.2 molar to 1.0 molar to about pH 7.2 to about pH 10.0 with an alkali metal or ammonium base. The maximum yield of the insulin crystals is at pH 8.2. Jackson further discloses that the presence of a preservative—phenol or methyl p-hydroxybenzoate—does not alter the nature or yield of the sodium or ammonium crystallization of insulin. Surprisingly, the pH and the presence of the preservative have a profound effect on the claimed process.

Table 1 demonstrates the effects of pH and preservative on the crystallization of $Lys^{B28}Pro^{B29}$-hI. In the experiments, the initial concentration of cation was held at 37.5 mM. The final concentration varied depending on the amount of cation required to adjust the pH. An indication of "none" indicates either no crystals or predominantly amorphous product was obtained. An indication of "crystal" indicates processable crystals were formed.

TABLE 1

| Cation initial/final (mM) | Preservative (mM) | pH | Cation | Observations |
|---|---|---|---|---|
| 37.5/575 | phenol (0.023 mM) | 9.0 | sodium | crystal |
| 37.5/514 | phenol (0.023 mM) | 8.2 | sodium | none |
| 37.5/514 | phenol (0.023 mM) | 8.5 | sodium | crystal |
| 37.5/591 | phenol (0.023 mM | 9.5 | sodium | crystal |
| 37.5/634 | phenol (0.023 mM | 10.0 | sodium | none |
| 37.5/576 | phenol (0.0077 mM | 9.0 | sodium | crystal |
| 37.5/576 | phenol (0.038 mM) | 9.0 | sodium | crystal |
| 37.5/606 | none | 9.0 | sodium | none |

The data disclosed in Table 1 demonstrate that preservative is a necessary element in the crystallization. The data further demonstrate the sensitivity of the crystallization to pH. The crystallization is carried out from about pH 8.5 to about pH 9.5.

Most unexpectedly, soluble $Lys^{B28}Pro^{B29}$-hI does not crystallize under the conditions for preparing insulin crystals. Table 2 presents a side-by-side comparison of human insulin in the commercial 8.2 process described in Jackson, U.S. Pat. No. 3,719,655, $Lys^{B28}Pro^{B29}$-hI in the 8.2 process, and $Lys^{B28}Pro^{B29}$-hI in the claimed process.

TABLE 2

| Protein (20 g/L) | Cation initial/final (mM) | Preservative (mM) | pH | Cation | Observations |
|---|---|---|---|---|---|
| Insulin | 250/725 | phenol[1] | 8.2 | sodium | cryatsl |
| $Lys^{B28}Pro$ | 253/728 | phenol[1] | 8.2 | sodium | none |

TABLE 2-continued

| Protein (20 g/L) | Cation initial/final (mM) | Preservative (mM) | pH | Cation | Observations |
|---|---|---|---|---|---|
| B29-hI Lys$^{B28}$Pro B29-hI | 37.5/575 | phenol[2] | 9.0 | sodium | crystal |

[1]Pehnol was added after the pH adjustment.
[2]Phenol added before the pH adjustment.

Lys$^{B28}$Pro$^{B29}$-hI can be prepared by any of a variety of recognized peptide synthesis techniques including classical (solution) methods, solid phase methods, semi synthetic methods, and more recent recombinant DNA methods. For example, Chance et al., U.S. patent application Ser. No. 07/388,201, EPO publication number 383 472, discloses the preparation of Lys$^{B28}$Pro$^{B29}$-human insulin.

The following examples are provided merely to further illustrate the preparation of the insulin analogs and the invention. The scope of the invention is not construed as merely consisting of the following examples. In the following examples, the final cation concentration was calculated by adding the initial cation content to the amount of cation added during pH adjustment and subsequent salt spiking. This total amount of cation divided by the final volume of the crystallization (initial solution plus volume added during pH adjustments) yields the final cation molarity.

EXAMPLE 1

Sample was prepared by combining 4 mL of a 25 mg/mL Lys$^{B28}$Pro$^{B29}$-hI solution with 0.1 mL glacial acetic acid, 0.81 mL purified water, and 0.094 mL 2M NaCl to produce a solution that was 20 mg/mL in protein, 37.5 mM NaCl, and 0.75M acetic acid. Liquefied phenol was added at 0.3% v/v of solution (0.023 mM). The pH was then raised to approximately 9.0 with 1.4 mL of 10% NaOH solution. This was then held at 5° C. with gentle agitation for 24 hours, well-defined crystals were observed.

EXAMPLE 2 AND 3

Two samples were prepared in a manner analogous to Example 1. Each sample was 37.5 mM in NaCl, 0.75M acetic acid, and 0.3% v/v liquefied phenol. However, one solution contained 10 mg/mL Lys$^{B28}$Pro$^{B29}$-hI, and the other contained 25 mg/mL Lys$^{B28}$Pro$^{B29}$-hI. The pH of each solution was adjusted to approximately 9.0 with 10% NaOH. Both samples were then held at 5° C. with gentle agitation for 24 hours, after which well-defined crystals were observed.

EXAMPLE 4 AND 5

Two samples were prepared in a manner analogous to Example 1. Each was 20 mg/mL protein, 37.5 mM in NaCl, and 0.75M acetic acid. However, one solution contained 0.1% v/v liquefied phenol and the other contained 0.5% liquefied phenol. The pH of each solution was adjusted to approximately 9.0 with 10% NaOH. Both samples were then held at 5° C. with gentle agitation for 24 hours, after which well-defined crystals were observed.

EXAMPLE 6, 7 AND 8

Samples were prepared in a manner analogous to Example 1. Each was 20 mg/mL protein, 0.75M acetic acid, and 0.3% v/v liquefied phenol. However, one was 25 mM NaCl; one was 50 mM NaCl; and one was 200 mM NaCl. The pH of each solution was adjusted to approximately 9.0 with 10% NaOH. Samples were held at 5° C. with gentle agitation for 24 hours. After this period of time, the solution with an initial 25 mM NaCl content remained clear with no crystals nor amorphous precipitate present. The solution with an initial 50 and 200 mM NaCl content contained well defined crystals, as well as amorphous precipitate.

EXAMPLE 9 AND 10

Two samples were prepared in a manner analogous to Example 1. Each was 20 mg/mL protein, 37.5 mM in NaCl, and 0.3% v/v liquefied phenol. However, one solution was of 0.5N acetic acid and the other was 1.0N acetic acid. The pH of each solution was adjusted to approximately 9.0 with 10% NaOH. Both samples were then held at 5° C. with gentle agitation for 24 hours. The crystallization that was carried out in 0.5N acetic acid produced well-defined crystals. The crystallization carried out in 1.0N acetic acid contained small crystals as well as amorphous precipitate.

EXAMPLE 11, 12, 13, AND 14

Samples were prepared in a manner analogous to Example 1. Each was 20 mg/mL protein, 37.5 mM in NaCl, 0.75N acetic acid, and 0.3% v/v liquefied phenol. The pH of each solution was adjusted with 10% NaOH to different values ranging from 8.2 to 10.0. All samples were then held at 5° C. with gentle agitation for 24 hours. The crystallization carried out at pH of approximately 8.2 produced neither crystals nor amorphous precipitate. The crystallization carried out at pH of approximately 8.5 produced poorly defined crystals as well as an amorphous precipitate. The crystallization carried out at pH of approximately 9.5 produced well-defined crystals. The crystallization carried out at pH of approximately 10.0 produced neither crystalline nor amorphous precipitate.

EXAMPLE 15

The crystallization described in Example 1 was repeated at a temperature of approximately 23° C. After gentle agitation for 24 hours at this temperature, well-defined crystals were observed.

EXAMPLE 16

The crystallization described in Example 1 was repeated in the absence of preservative. After gentle agitation for 24 hours at 5° C., neither crystalline nor amorphous precipitate was observed.

EXAMPLE 17

The crystallization described in Example 1 was repeated using human insulin rather than Lys$^{B28}$Pro$^{B29}$-hI. At a pH of approximately 9.0, the solution was milky white indicating the presence of amorphous precipitate. This was confirmed by microscopic examination. After gentle agitation for 24 hours at 5° C., the solution still contained only amorphous precipitate.

EXAMPLE 18

The crystallization described in Example 1 was repeated with the exception that the preservative addition was after the pH had been adjusted to approximately 9.0. After gentle agitation for 24 hours at 5° C., a predominantly amorphous precipitate and isolated crystals were observed. The material was not suitable for further processing.

EXAMPLE 19, 20, AND 21

The crystallization described in Example 1 was repeated using various preservatives. Each preservative was added to the crystallization solution at a concentration of 0.023 mM. The preservatives used were meta-cresol, resorcinol, and methyl paraben. After gentle agitation for 24 hours at 5° C., crystals were observed in each of the samples. The crystallization carried out in the presence of meta-cresol produced crystals that were oblong rectangles that exhibited twinning behavior. The crystals produced in the presence of resorcinol were plate-like in nature, and those produced in the presence of methyl paraben octahedral in shape.

EXAMPLE 22 AND 23

The crystallization described in Example 1 was repeated using cations other than sodium. Each solution was 20 mg/mL, 0.75N acetic acid, 0.3% v/v liquefied phenol, and 37.5 mM in the chloride salt of the cation of either potassium or ammonium. The pH of each solution was adjusted to approximately 9.0 using either 10% KOH or concentrated ammonium hydroxide solution. After gentle agitation for 24 hours at 5° C., crystals were observed in each sample.

EXAMPLE 24 AND 25

Samples of $Lys^{B28}Pro^{B29}$-hI in 0.5N acetic acid were diafiltered to perform a buffer exchange into either 0.1M citric acid or 0.1M phosphoric acid. Each solution was then used to perform a crystallization that was 20 mg/mL in protein, 37.5 mM NaCl, and 0.3% v/v liquefied phenol. The pH of each solution was adjusted to approximately 9.0 using 10% NaOH. After gentle agitation for 24 hours at 5° C., no crystals were observed in either sample. Additional quantities of NaCl were added to the solutions (0.4 mL of 4M NaCl in the phosphate sample and 0.3 mL of 4M NaCl in the citrate sample). The solutions were agitated for 24 hours. Uniform crystals were observed in both solutions.

EXAMPLE 26

A crystallization was prepared using the process described in Jackson, U.S. Pat. No. 3,719,655, the pH 8.2 procedure. A 5 mL sample was prepared that was 20 mg/mL $Lys^{B28}Pro^{B29}$-hI in 0.75N acetic acid. To this solution, sodium edetate was added as a quantity of 8 g/l. To this solution, 0.05 g of NaCl were added. The pH of this solution was adjusted to 8.4 using a 10% NaOH solution. To this solution, liquefied phenol was added at 3.3 mL/L. Additional NaCl, 0.025 g, was added to the solution. The final pH of the solution was 8.22. After agitation at room temperature for 1 hour, no crystals were observed, only amorphous precipitate.

EXAMPLE 27

A process stream 99.7 base grams of $Lys^{B28}Pro^{B29}$-human insulin in 5.68 L of acetic acid buffer was diluted to an absorbance at 276 nm of 20.1 with acetic acid/salt solution (1.32 L of solution prepared by combining 5 L of water with 0.215 L of glacial acetic acid and 11 grams of sodium chloride) in a glass container. The material was filtered through a 0.2 micron filter. Liquefied phenol was added to the solution at 3.3 mL/L (22.6 mL total), and the pH of the resulting solution was confirmed to be below pH 3. The solution was adjusted to pH 8.99 by the addition of 1.75 L of sodium hydroxide (10% solution w/v). The solution was then gently agitated at 2°–8° C. for 15 minutes, agitation was stopped and resulting crystals were allowed to settle for 24 hours. After the crystals had settled, 6.2 L of the supernatant was decanted, the crystals were slurried in the remaining volume and centrifuged in a one liter centrifuge bottle at 4000 rpm (approximately 4000×G) in a DPR6000 centrifuge for 10–20 minutes. The centrate was decanted. The crystals (approximately 350 mL packed bed) were slurried with 1.3 L of 1M sodium acetate and recentrifuged at 4000 rpm for 10–20 minutes. The crystals were then added with agitation to approximately 11 L of chilled (2°–8° C.) Alcohol SD No. 3A Absolute and recentrifuged at 4000 rpm for 15 minutes. The alcohol centrate was decanted, and the alcohol wash was repeated twice more. The alcohol washed crystals (292 grams wet weight) were dried under vacuum. Total yield was greater than 90%. Subsequent analysis by several techniques indicated the crystallization procedure did not alter the purity or aggregation kinetics of the material.

We claim:
1. A process for preparing a crystalline $Lys^{B28}Pro^{B29}$-human insulin alkali metal or ammonium salt, which comprises adjusting the pH of a solution from a pH below the isoelectric point of $Lys^{B28}Pro^{B29}$-human insulin to between about pH 8.5 to about pH 9.5 with an alkali metal or ammonium base; wherein said solution comprises about 5 mg/mL to about 50 mg/mL $Lys^{B28}Pro^{B29}$-human insulin, a pharmaceutically acceptable preservative, and an initial cation concentration of about 30 mM to about 100 mM said cation being selected from the group consisting of an alkali metal or ammonium.

2. The process of claim 1, wherein the alkali metal is sodium or potassium.

3. The process of claim 1, wherein the cation is sodium.

4. The process of claim 1, wherein the cation is ammonium.

5. The process of claim 3, wherein the pH is adjusted to 8.9 to 9.1.

6. The process of claim 5, wherein the solution further comprises a buffer selected from acetate, phosphate, or citrate.

7. The process of claim 6, wherein the buffer is acetate.

8. The process of claim 7, wherein the concentration of $Lys^{B28}Pro^{B29}$-human insulin is about 18 mg/mL to about 22 mg/mL.

9. The process of claim 8, wherein the preservative is phenol.

* * * * *